United States Patent [19]

Sakane et al.

[11] Patent Number: 4,952,578
[45] Date of Patent: Aug. 28, 1990

[54] CEPHEM COMPOUND AND A PROCESS FOR PREPARATION THEREOF

[75] Inventors: Kazuo Sakane, Kawanishi; Kohji Kawabata, Osaka; Kenzi Miyai, Kawanishi; Yoshiko Inamoto, Toyonaka, all of Japan

[73] Assignee: Fujisawa Pharmaceutical Co., Ltd., Osaka, Japan

[21] Appl. No.: 241,419

[22] Filed: Sep. 7, 1988

[30] Foreign Application Priority Data

Sep. 14, 1987 [GB] United Kingdom ............ 8721568
Jun. 28, 1988 [GB] United Kingdom ............ 8815361

[51] Int. Cl.$^5$ ............... C07D 501/46; A61K 31/545
[52] U.S. Cl. .................................... 514/202; 540/222
[58] Field of Search ..................... 540/222; 514/202

[56] References Cited

U.S. PATENT DOCUMENTS 4,401,668 8/1983 Lunn .................................. 540/222

FOREIGN PATENT DOCUMENTS 223246A 11/1985 European Pat. Off. .

Primary Examiner—Anton H. Sutto
Assistant Examiner—C. L. Cseh
Attorney, Agent, or Firm—Oblon, Spivak, McClelland, Maier & Neustadt

[57] ABSTRACT

The object of the invention is a new cephem compound with antimicrobial activity used for the treatment of infectious diseases of the general formula:

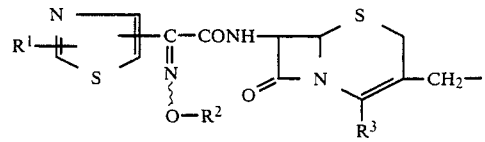

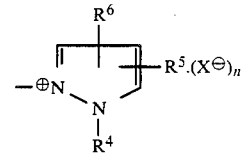

wherein
$R_1$ is amino or a protected amino
$R_2$ is lower alkyl which may have 1 to 3 halogens
$R_3$ is $COO^\ominus$, carboxy or a protected carboxy
$R_4$ is hydroxy(lower)alkyl or protected hydroxy(lower)alkyl
$R_5$ is amino or a protected amino
$R_6$ is hydrogen or lower alkyl
$X^\ominus$ is an anion, and
$n$ is 0 or 1 with proviso that
(i) when $R_3$ is $COO^\ominus$, then n is 0, and
(ii) when $R_3$ is carboxy or a protected carboxy, then n is 1, and pharmaceutically acceptable salt thereof.

8 Claims, No Drawings

CEPHEM COMPOUND AND A PROCESS FOR PREPARATION THEREOF

The present invention relates to new cephem compound and a pharmaceutically acceptable salt thereof.

More particularly, it relates to new cephem compound and a pharmaceutically acceptable salt thereof, which have antimicrobial activities, to a process for preparation thereof, to pharmaceutical composition comprising the same, and to a method for treating infectious diseases in human being or animals.

Accordingly, one object of the present invention is to provide the cephem compound and a pharmaceutically acceptable salt thereof, which are highly active against a number of pathogenic microorganisms.

Another object of the present invention is to provide a process for the preparation of the cephem compound or a salt thereof.

A further object of the present invention is to provide a pharmaceutical composition comprising, as an active ingredient, said cephem compound or a pharmaceutically acceptable salt thereof.

Still further object of the present invention is to provide a method for treating infectious diseases caused by pathogenic microorganisms, which comprises administering said cephem compound to infected human being or animals.

The object cephem compound is novel and can be represented by the following general formula [I]:

[structural formula I]

wherein
$R^1$ is amino or a protected amino,
$R^2$ is lower alkyl which may have one or more suitable substituent(s),
$R^3$ is $COO^{\oplus}$, carboxy or a protected carboxy,
$R^4$ is hydroxy(lower)alkyl or protected hydroxy(lower)alkyl,
$R^5$ is amino or a protected amino,
$R^6$ is hydrogen or lower alkyl,
$X^{\ominus}$ is an anion, and
n is 0 or 1,
with proviso that
(i) when $R^3$ is $COO^{\ominus}$, then n is 0, and
(ii) when $R^3$ is carboxy or a protected carboxy, then n is 1.

As to the object compound [I], the following points are to be noted.

That is, the object compound [I] includes syn isomer, anti isomer and a mixture thereof. Syn isomer means one geometrical isomer having the partial structure represented by the following formula:

[structural formula]

(wherein $R^1$ and $R^2$ are each as defined above), and anti isomer means the other geometrical isomer having the partial structure represented by the following formula:

[structural formula]

(wherein $R^1$ and $R^2$ are each as defined above), and all of such geometrical isomers and mixture thereof are included within the scope of this invention.

In the present specification and claim, the partial structure of these geometrical isomers and mixture thereof are represented for convenient sake by the following formula:

[structural formula]

(wherein $R^1$ and $R^2$ are each as defined above).

Another point to be noted is that the pyrazolic moiety of the compound [I] can also exist in the tautomeric form, and such tautomeric equilibrium can be represented by the following scheme.

[structural formulas (A) and (B)]

(wherein $R^4$, $R^5$ and $R^6$ are each as defined above).

Both of the above tautomeric isomers are included within the scope of the present invention, and in the present specification and claim, however, the object compound [I] is represented for the convenient sake by one expression of the pyrazolic group of the formula (A).

The cephem compound [I] of the present invention can be prepared by processes as illustrated in the following reaction schemes.

Process 1

-continued
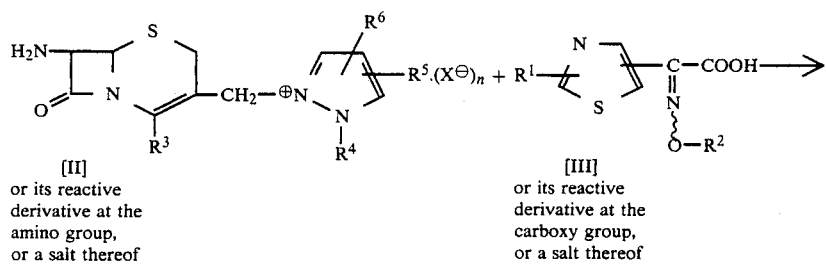
[II]
or its reactive
derivative at the
amino group,
or a salt thereof
[III]
or its reactive
derivative at the
carboxy group,
or a salt thereof
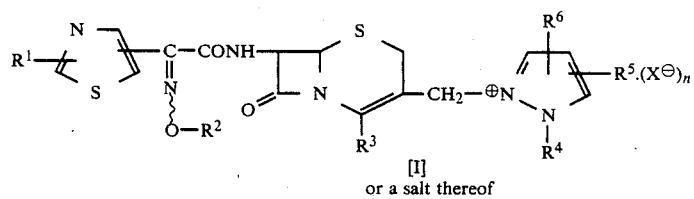
[I]
or a salt thereof
Process 2
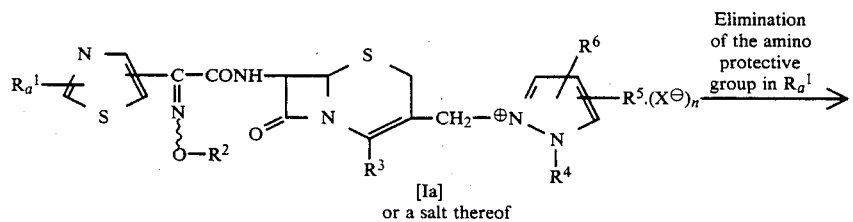
[Ia]
or a salt thereof
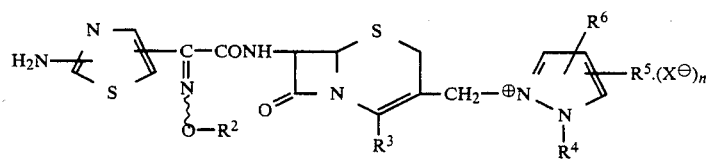
[Ib]
or a salt thereof
Process 3
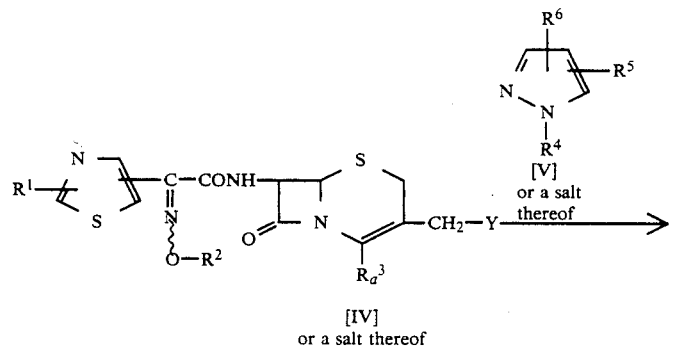
[IV]
or a salt thereof
[V]
or a salt thereof
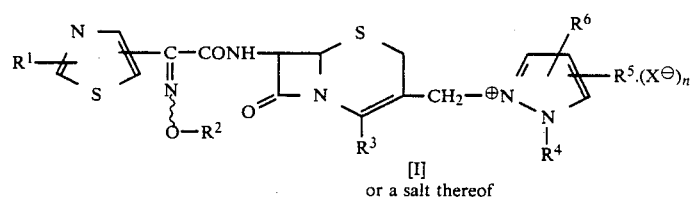
[I]
or a salt thereof
Process 4

-continued

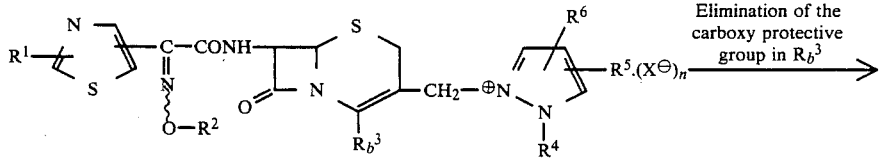

[Ic] or a salt thereof

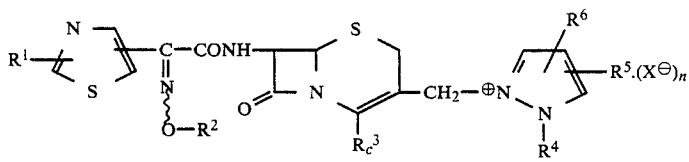

[Id] or a salt thereof

Process 5

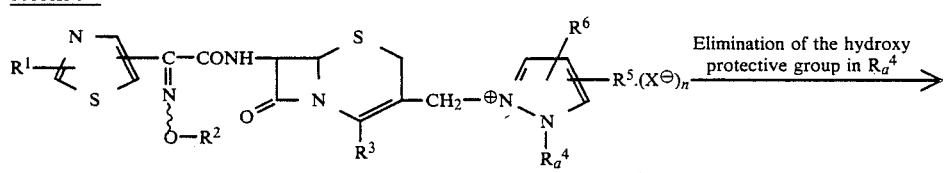

[Ie] or a salt thereof

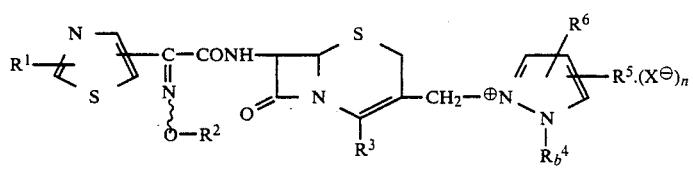

[If] or a salt thereof

Process 6

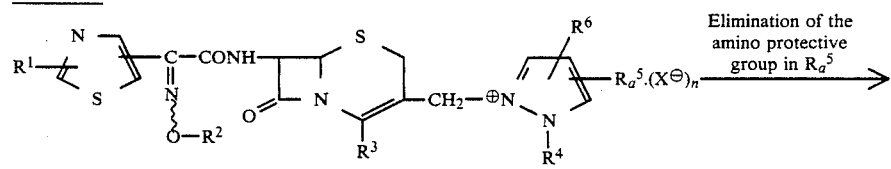

[Ig] or a salt thereof

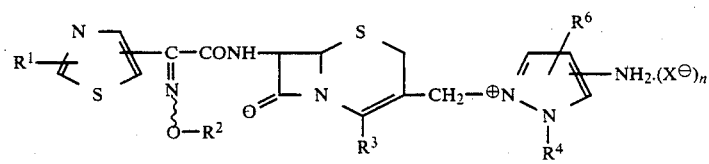

[Ih] or a salt thereof wherein
$R^1$, $R^2$, $R^3$, $R^4$, $R^5$, $R^6$, $X^\ominus$ and n are each as defined above
$R_a^1$ is a protected amino,
$R_a^3$ is carboxy or a protected carboxy,
$R_b^3$ is a protected carboxy,
$R_c^3$ is $COO^\ominus$ or carboxy,
$R_a^4$ is protected hydroxy (lower) alkyl,
$R_b^4$ is hydroxy (lower) alkyl,
$R_a^5$ is a protected amino, and Y is a leaving group.

The starting compound [II] or a salt thereof is novel and can be prepared according to the following reaction schemes.

Process A

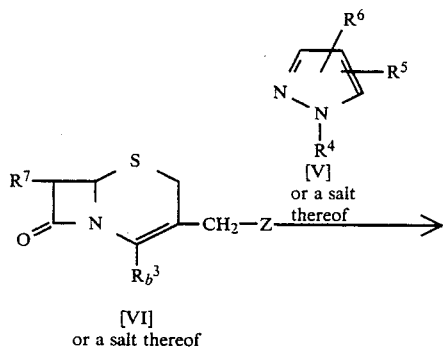

wherein
R³, R$_b$³, R$_c$³, R⁴, R$_a$⁴, R$_b$⁴, R⁵, R$_a$⁵, R⁶, X⊖ and n are each as defined above,
R⁷ is a protected amino, and
Z is a leaving group.

Some of the starting compound [V] or a salt thereof are novel and they can be prepared according to the methods disclosed in Preparations described later or similar manners thereto.

Suitable pharmaceutically acceptable salts of the object compound [I] are conventional non-toxic mono or di salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N-dibenzylethylenediamine salt, etc.], an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, hydroiodide, sulfate, phosphate, etc.], a salt with an amino acid [e.g. arginine salt, aspartic acid salt, glutamic acid salt, etc.], and the like.

In the above and subsequent descriptions of this specification, suitable examples of the various definitions are explained in detail as follows:

The term "lower" is intended to mean 1 to 6 carbon atom(s), unless otherwise indicated.

Suitable protective group in "a protected amino" may include ar(lower)alkyl such as mono or di or triphenyl(lower)alkyl [e.g. benzyl, phenethyl, 1-phenylethyl, benzhydryl, trityl, etc.], acyl as explained hereinbelow, and the like.

Suitable acyl may be aliphatic acyl, aromatic acyl, arylaliphatic acyl and heterocyclic-aliphatic acyl derived from carboxylic acid, carbonic acid, carbamic acid, sulfonic acid, and the like.

Suitable example of the acyl group thus explained may be lower alkanoyl [e.g. formyl, acetyl, propionyl, hexanoyl, pivaloyl, etc.], mono(or di or tri)halo(lower)alkanoyl [e.g. chloroacetyl, trifluoroacetyl, etc.], lower alkoxycarbonyl [e.g. methoxycarbonyl, ethoxycarbonyl, tert-butoxycarbonyl, tert-pentyloxycarbonyl, hexyloxycarbonyl, etc.], mono(or di or tri)halo(lower)alkoxycarbonyl [e.g. chloromethoxy carbonyl, dichloroethoxycarbonyl, trichloroethoxycarbonyl, etc.], aroyl [e.g. benzoyl, toluoyl, xyloyl, naphthoyl, etc.], ar(lower)alkanoyl such as phenyl(lower)alkanoyl [e.g. phenylacetyl, phenylpropionyl, etc.], aryloxycarbonyl [e.g. phenoxycarbonyl, naphthyloxycarbonyl, etc.], aryloxy(lower)alkanoyl such as phenoxy(lower)alkanoyl [e.g. phenoxyacetyl, phenoxypropionyl, etc.], arylglyoxyloyl [e.g. phenylglyoxyloyl, naphthylglyoxyloyl, etc.], ar(lower)alkoxycarbonyl which may have suitable substituent(s) such as phenyl(lower)alkoxycarbonyl which may have nitro or lower alkoxy [e.g. benzyloxycarbonyl, phenethyloxycarbonyl, p-nitrobenzyloxycarbonyl, p-methoxybenzyloxycarbonyl, etc.], thienylacetyl, imidazolylacetyl, furylacetyl, tetrazolylacetyl, triazolylacetyl, thiadiazolylacetyl, thienylpropionyl, thiadiazolylpropionyl, lower alkylsulfonyl [e.g. methylsulfonyl, ethylsulfonyl, propylsulfonyl, isopropylsulfonyl, pentylsulfonyl, butylsulfonyl, etc.], arylsulfonyl [e.g. phenylsulfonyl, tolylsulfonyl, xylylsulfonyl, naphthylsulfonyl, etc.], ar(lower)alkylsulfonyl such as phenyl(lower)alkylsulfonyl [e.g. benzylsulfonyl, phenethylsulfonyl, benzhydrylsulfonyl, etc.], and the like.

Preferable example of "a protected amino" thus defined may be ar(lower)alkylamino and lower alkanoylamino, more preferable one may be triphenyl-($C_1$–$C_4$)alkylamino and $C_1$–$C_4$ alkanoylamino, and the most preferable one may be tritylamino, formamido and acetamido.

Suitable "a protected carboxy" may be an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc.], lower alkanesulfonyl(lower)alkyl ester [e.g. 2-mesylethyl ester, etc.] or mono(or di or tri)halo(lower)alkyl ester [e.g. 2-iodoethyl ester, 2,2,2-trichloroethyl ester, etc.]; lower alkenyl ester [e.g. vinyl ester, allyl ester, etc.]; lower alkynyl ester [e.g. ethynyl ester, propynyl ester, etc.]; ar(lower)alkyl ester which may have suitable substituent(s) [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.]; aryl ester which may have suitable substituent(s) [e.g. phenyl ester, 4-chlorophenyl ester, tolyl ester, 4-tert-butylphenyl ester, xylyl ester, mesityl ester, cumenyl ester, etc.]; or the like, in which the preferred one may be mono or di or triphenyl($C_1$–$C_4$)alkyl ester and the most preferred one may be benzhydryl ester.

Suitable "lower alkyl" may be straight or branched ones such as methyl, ethyl, propyl, isopropyl, butyl, t-butyl, pentyl, 2-ethylpropyl, hexyl or the like, in which the preferred "lower alkyl" may be ($C_1$–$C_4$)alkyl and the most preferred one may be methyl.

Suitable examples of "suitable substituent(s)" in "lower alkyl which may have one or more suitable substituent(s)" may include halogen [e.g. fluoro, chloro, bromo, iodo] and the like.

Suitable examples of said lower alkyl having one or more suitable substituent(s) may include lower alkyl having one or more halogen such as fluoromethyl, difluoromethyl, trifluoromethyl, 2-fluoroethyl, 2-chloro-2-fluoroethyl, 3-bromo-2-fluoropropyl, 1-chloromethyl-2-iodo-1-bromoethyl, 2-difluorobutyl, 1-dichloromethyl-1-methylethyl, 2-fluoro-4-chloro-5-bromopentyl, 1-difluoro-2-ethylpropyl, 2-fluoro-3-iodohexyl or the like, and the like, in which the preferred one may be ($C_1$–$C_4$)alkyl having 1 to 3 halogen, the more preferred one may be dihalo($C_1$–$C_4$)alkyl and the most preferred one may be difluoromethyl.

Suitable "hydroxy(lower)alkyl" may include hydroxymethyl, 1-hydroxyethyl, 2-hydroxyethyl, 3-hydroxypropyl, 1-(hydroxymethyl)ethyl, 1-hydroxybutyl, 1-hydroxymethyl-1-methylethyl, 3-hydroxypentyl, 3-hydroxy-2-ethylpropyl, 6-hydroxyhexyl and the like, in which the preferred one may be hydroxy($C_1$–$C_4$)alkyl and the most preferred one may be 2-hydroxyethyl.

Suitable "protected hydroxy(lower)alkyl" may include acyloxy(lower)alkyl and the like, in which suitable "acyl" moiety can be referred to the ones as exemplified for "a protected amino" before and suitable examples of said "acyloxy(lower)alkyl may be lower alkanoyloxy(lower)alkyl [e.g. formyloxymethyl, 1-formyloxyethyl, 2-formyloxyethyl, 2-acetoxyethyl, 3-acetoxypropyl, 1-(propionyloxymethyl)ethyl, 1-butyryloxybutyl, 1-hexanoyloxybutyl, 1-pivaloyloxymethyl-1-methylethyl, 3-formyloxypentyl, 3-formyloxy-2-ethylpropyl, 6-acetoxyhexyl, etc.], carbamoyloxy(lower)alkyl [e.g. carbamoyloxymethyl, 1-carbamoyloxyethyl, 2-carbamoyloxyethyl, 3-carbamoyloxypropyl, 1-(carbamoyloxymethyl)ethyl, 1-carbamoyloxybutyl, 1-carbamoyloxymethyl-1-methylethyl, 3-carbamoyloxypentyl, 3-carbamoyloxy-2-ethylpropyl, 6-carbamoyloxyhexyl, etc.] or the like; in which the preferred one may be ($C_1$–$C_4$)-alkanoyloxy($C_1$–$C_4$)alkyl or carbamoyloxy($C_1$–$C_4$)alkyl and the most preferred one may be 2-formyloxyethyl, 2-acetoxyethyl or 2-carbamoyloxyethyl.

Suitable "anion" may be formate, acetate, trifluoroacetate, maleate, tartrate, methanesulfonate, benzenesulfonate, toluenesulfonate, chloride, bromide, iodide, sulfate, phosphate, or the like.

Suitable "a leaving group" may be halogen [e.g. chlorine, bromine, iodine, etc.], acyloxy such as sulfonyloxy [e.g. benzenesulfonyloxy, tosyloxy, mesyloxy, etc.], lower alkanoyloxy [e.g. acetyloxy, propionyloxy, etc.], or the like.

The processes for preparing the object compound of the present invention are explained in detail in the following.

Process 1

The object compound [I] or a salt thereof can be prepared by reacting a compound [II] or its reactive derivative at the amino group or a salt thereof with a compound [III] or its reactive derivative at the carboxy group or a salt thereof.

Suitable reactive derivative at the amino group of the compound [II] may include Schiff's base type imino or its tautomeric enamine type isomer formed by the reaction of the compound [II] with a carbonyl compound such as aldehyde, ketone or the like; a silyl derivative formed by the reaction of the compound [II] with a silyl compound such as bis(trimethylsilyl)acetamide, mono(trimethylsilyl)acetamide, bis(trimethylsilyl)urea or the like; a derivative formed by reaction of the compound

[II] with phosphorus trichloride or phosgene, and the like.

Suitable salts of the compound [II] and its reactive derivative can be referred to the ones as exemplified for the compound [I].

Suitable reactive derivative at the carboxy group of the compound [III] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid; sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g. cyanomethyl ester, methoxymethyl ester, dimethyliminomethyl $[(CH_3)_2N^+=CH-]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound [III] to be used.

Suitable salts of the compound [III] and its reactive derivative can be referred to the ones as exemplified for the compound [I].

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [III] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 2

The object compound [Ib] or a salt thereof can be prepared by subjecting a compound [Ia] or a salt thereof to elimination reaction of the amino protective group in $R_a^1$.

This reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.]and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reaction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g.

reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the abovementioned acids to be used in chemical reduction are in liquid, they can also be used as a solvent. Further, a suitable solvent to be used in catalytic reduction may be the abovementioned solvent, and other conventional solvent such as diethyl ether, dioxane, tetrahydrofuran, etc., or a mixture thereof.

The reaction temperature of this reduction is not critical and the reaction is usually carried out under cooling to warming.

The present invention includes within the scope of the invention the case that a protected amino in $R^5$ is transformed into amino, the case that a protected carboxy in $R^3$ is transformed into carboxy and the case that protected hydroxy(lower)alkyl in $R^4$ is transformed into hydroxy(lower)alkyl.

Process 3

The object compound [I] or a salt thereof can be prepared by reacting a compound [IV] or a salt thereof with a compound [V] or a salt thereof.

Suitable salts of the compounds [IV] can be referred to the ones as exemplified for the compound [I].

Suitable salts of the compounds [V] may be an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], or the like.

The present reaction may be carried out in a solvent such as water, phosphate buffer, acetone, chloroform, acetonitrile, nitrobenzene, methylene, chloride, ethylene chloride, formamide, N,N-dimethylformamide, methanol, ethanol, diethyl ether, tetrahydrofuran, dimethyl sulfoxide, or any other organic solvent which does not adversely affect the reaction, preferably in ones having strong polarities. Among the solvents, hydrophilic solvents may be used in a mixture with water. When the compound [V] is in liquid, it can also be used as a solvent. The reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under heating. The present reaction is preferably carried out in the presence of alkali metal halide [e.g. sodium iodide, potassium iodide, etc.], alkali metal thiocyanate [e.g. sodium thiocyanate, potassium thiocyanate, etc.] or the like.

Anion $X^\ominus$ may be the one derived from a leaving group Y and may be the other one converted therefrom by a conventional method.

Process 4

The object compound [Id] or a salt thereof can be prepared by subjecting a compound [Ic] or a salt thereof to elimination reaction of the carboxy protective group in $R_b^3$.

This reaction can be carried out in a similar manner to that of Process 2 mentioned in the above, and therefore the reaction mode and reaction conditions [e.g. base, acid, catalyst, solvent, reaction temperature, etc.] of this reaction are to be referred to those as explained in Process 2.

The present invention includes within the scope of the invention the cases that a protected amino in $R^1$ and/or $R^5$ and/or protected hydroxy(lower)alkyl in $R^4$ are transformed into amino and/or hydroxy(lower)alkyl, respectively during this reaction.

Process 5

The object compound [If] or a salt thereof can be prepared by subjecting a compound [Ie] or a salt thereof to elimination reaction of the hydroxy protective group in $R_a^4$.

This reaction can be carried out in a similar manner to that of Process 2 mentioned in the above, and therefore the reaction mode and reaction conditions [e.g. base, acid, catalyst, solvent, reaction temperature, etc.] of this reaction are to be referred to those as explained in Process 2.

The present invention includes within the scope of the invention the cases that a protected amino in $R^1$ and/or $R^5$, and/or a protected carboxy in $R^3$ are transformed into amino, and/or carboxy, respectively during this reaction.

Process 6

The object compound [Ih] or a salt thereof can be prepared by subjecting a compound [Ig] or a salt thereof to elimination reaction of the amino protective group in $R_a^5$.

This reaction can be carried out in a similar manner to that of Process 2 mentioned in the above, and therefore the reaction mode and reaction conditions [e.g. base, acid, catalyst, solvent, reaction temperature, etc.] of this reaction are to be referred to those as explained in Process 2.

The present invention includes within the scope of the invention the case that a protected amino in $R^1$, and/or a protected carboxy in $R^3$, and/or protected hydroxy(lower)alkyl in $R^4$ are transformed into amino, and/or carboxy, and/or hydroxy(lower)alkyl, respectively during this reaction.

The reactions in Processes A to C for preparing the starting compound [II] or a salt thereof can be carried out according to the similar manners to those explained in Processes 2 to 6 for preparing the compound [I] or a salt thereof.

Now in order to show the utility of the object compound [I], the test data on MIC (minimal inhibitory concentration) of representative compound [I] of this invention is shown in the following.

Test Method:

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of $\mu$g/ml after incubation at 37° C. for 20 hours.

Test Compound (1)

7β-[2-(2-Aminothiazol-4-yl)-2-methox-
yiminoacetamido]-3-[3-amino-2-(2-hydroxyethyl)-1-
pyrazolio]methyl-3-cephem-4-carboxylate (syn isomer)
(the compound of Example 4)

Test Result

| | MIC (μg/ml) |
|---|---|
| Test Bacteria | Test Compound (1) |
| *P. aeruginosa* 26 | 0.39 |

For therapeutic administration, the object compound [I] and a pharmaceutically acceptable salt thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound [I] may vary from and also depend upon the age, conditions of the patient, a kind of diseases, a kind of the compound [I] to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compound [I] of the present invention may be used in treating diseases infected by pathogenic microorganisms.

The following Preparations and Examples are given for the purpose of illustrating the present invention in more detail.

Preparation 1

A mixture of acetic anhydride (11.13 ml) and formic acid (5.93 ml) was stirred at ambient temperature for 30 minutes. To this solution was added 5-amino-1-(2-hydroxyethyl)pyrazole (5 g) under ice-cooling, and the mixture was stirred at 30°-40° C. for 1 hour. The reaction mixture was poured into a mixture of water, tetrahydrofuran and ethyl acetate and adjusted to pH 6 with aqueous sodium bicarbonate. The organic layer was separated, and the aqueous layer was extracted with a mixture of tetrahydrofuran and ethyl acetate for three times. The organic layers were combined, dried over magnesium sulfate and evaporated in vacuo to give 5-formamido-1-(2-formyloxyethyl)pyrazole (5.18 g).

IR (Nujol): 3180, 1705, 1660 cm$^{-1}$

NMR (DMSO-$d_6$, δ): 4.21–4.61 (4H, m), 6.11 and 6.34 (1H, each d, J=3 Hz), 7.47 (1H, d, J=3 Hz), 8.00 (1H, s), 8.33 (1H, s)

Preparation 2

To a mixture of benzhydryl 7β-tert-butoxycarbonylamino-3-chloromethyl-3-cephem 4-carboxylate (20 g) and sodium iodide (5.82 g) in N,N-dimethylformamide (20 ml) was added 5-formamido-1-(2-formyloxyethyl)pyrazole (21.34 g) at ambient temperature. After being stirred for 24 hours at the same temperature, the mixture was poured into a mixture of water and ethyl acetate. The organic layer was separated and washed with water, aqueous sodium chloride solution, and dried over magnesium sulfate. The solution was evaporated in vacuo to give benzhydryl 7β-tert-butoxycarbonylamino-3-[3-formamido-2-(2-formyloxyethyl)-1-pyrazolio]methyl-3-cephem-4-carboxylate iodide (29.6 g).

IR (Nujol): 1780, 1720 cm$^{-1}$

NMR (DMSO-$d_6$, δ) 1.49 (9H, s), 3.43 (2H, broad s), 4.14–4.38 (2H, m), 4.52–4.73 (2H, m), 5.15 (1H, d, J=5 Hz), 5.40 (2H, broad s), 5.67 (1H, dd, J=5 Hz and 8 Hz), 6.88 (1H, s), 7.02 (1H, d, J=3 Hz), 7.18–7.52 (10H, m), 7.94 (1H, d, J=8 Hz), 7.99 (1H, s), 8.27 (1H, d, J=3 Hz), 8.51 (1H, broad s)

Preparation 3

To a solution of benzhydryl 7β-tert-butoxycarbonylamino-3-[3-formamido-2-(2-formyloxyethyl)-1-pyrazolio]-methyl-3-cephem-4-carboxylate iodide (29.5 g) and anisole (30 ml) in methylene chloride (90 ml) was added dropwise trifluoroacetic acid (60 ml) under ice-cooling. After being stirred for 1 hour at ambient temperature, the mixture was poured into a mixture of diisopropyl ether (600 ml) and ethyl acetate (600 ml). The resultant precipitate was collected by filtration to give bis(trifluoroacetic acid salts) of 7β-amino-3-[3-formamido-2-(2-formyloxyethyl)-1-pyrazolio]methyl-3-cephem-4-carboxylate (22.7 g).

IR (Nujol): 1780, 1715, 1660 cm$^{-1}$

NMR (DMSO-$d_6$, δ): 3.53 (2H, broad s), 4.28–4.56 (2H, m), 4.78–4.99 (2H, m), 5.29 (2H, broad s), 5.53 (2H, broad s), 7.14 (1H, d, J=3 Hz), 8.22 (1H, s), 8.46 (1H, d, J=3 Hz), 8.63 (1H, s)

Preparation 4

Concentrated hydrochloric acid (5.67 ml) was added to a mixture of bis(trifluoroacetic acid salts) of 7β-amino-3-[3-formamido-2-(2-formyloxyethyl)-1-pyrazolio]methyl-3-cephem-4-carboxylate (10 g) in methanol (50 ml) at ambient temperature. After being stirred at the same temperature for 3 hours, the mixture was added dropwise to ethyl acetate (500 ml). The resultant precipitate was collected by filtration to give 7β-amino-3-[3-amino-2-(2-hydroxyethyl)-1-pyrazolio]-methyl-3-cephem-4-carboxylate trihydrochloride (6.1 g).

IR (Nujol): 3250, 1770, 1700, 1625 cm$^{-1}$

NMR (DMSO-$d_6$, δ): 3.43 (2H, broad s), 3.52–3.88 (2H, m), 4.18–4.48 (2H, m), 5.28 (2H, broad s), 5.37 (2H, broad s), 5.97 (1H, d, J=3 Hz), 8.18 (1H, d, J=3 Hz)

EXAMPLE 1

A mixture of N,N-dimethylformamide (0.41 ml) and phosphoryl chloride (0.49 ml) in ethyl acetate (2 ml) was stirred under ice-cooling for 30 minutes to prepare Vilsmeier reagent. 2-(2-Formamidothiazol-4-yl)-2-methoxyiminoacetic acid (1.02 g) was added to the above solution at 0°–5° C., and the mixture was stirred at the same temperature for 30 minutes to produce an activated acid solution. This activated acid solution was added to a solution of 7β-amino-3-[3-amino-2-(2-hydroxyethyl)-1pyrazolio]methyl-3-cephem-4-carboxylate trihydrochloride (2 g) and N-(trimethylsilyl)acetamide (5.85 g) in tetrahydrofuran (40 ml) under ice-cooling, and then the mixture was stirred at 10°–15° C. for 1 hour. The resultant mixture was poured into diethyl ether (500 ml), and the resulting precipitates were collected by filtration to give 7β-[2-(2-formamidothiazol-4-yl)-2-methoxyiminoacetamido]-3-[3-amino-2-(2-hydroxyethyl)-1-pyrazolio]-methyl-3-cephem-4-carboxylate dihydrochloride (syn isomer) (2.55 g).

IR (Nujol): 1770, 1660 cm$^{-1}$

NMR (DMSO-$d_6$, δ): 3.30 (2H, m), 3.68 (2H, 3.92 (3H, s), 4.31 (2H, m), 5.29 (1H, d, J=5 Hz), 5.32 (2H, m), 5.88 (1H, dd, J=5 Hz and 8 Hz), 5.99 (1H, d, J=3 Hz), 7.48 (1H, s), 8.12 (1H, d, J=3 Hz), 8.59 (1H, s), 9.81 (1H, d, J=8 Hz)

The following compounds (Examples 2 and 3) were prepared according to a similar manner to that of Example 1.

EXAMPLE 2

7β-[2-(2-Aminothiazol-4-yl)-2-methoxyiminoacetamido]-3-[3-amino-2-(2-hydroxyethyl)-1-pyrazolio]methyl-3-cephem-4-carboxylate (syn isomer)

IR (Nujol): 3300, 1770, 1640 cm$^{-1}$

EXAMPLE 3

7β-[2-(2-Aminothiazol-4-yl)-2-(difluoromethoxyimino)-acetamido]-3-[3-amino-2-(2-hydroxyethyl)-1-pyrazolio]-methyl-3-cephem-4-carboxylate (syn isomer)

IR (Nujol): 3300, 1760, 1660 cm$^{-1}$

EXAMPLE 4

To a solution of 7β-[2-(2-formamidothiazol-4-yl)-2-methoxyiminoacetamido]-3-[3-amino-2-(2-hydroxyethyl)-1pyrazolio]methyl-3-cephem-4-carboxylate dihydrochloride (syn isomer) (2.5 g) in methanol (12.5 ml) was added concentrated hydrochloric acid (0.88 ml) at ambient temperature. After being stirred at the same temperature for 2 hours, the mixture was poured into ethyl acetate (500 ml), and the resulting precipitate was collected by filtration. The precipitate was dissolved in water (100 ml), and adjusted to pH 2 with 5% aqueous sodium bicarbonate solution. This solution was subjected to column chromatography on macroporous non-ionic adsorption resin "Diaion HP-20" (Trademark, manufactured by Mitsubishi Chemical Industries). The object compound was eluted with 10% diisopropyl alcohol, and lyophilized to give 7β-[2-(2-aminothiazol-4-yl)-2-methoxyiminoacetamido]-3-[3-amino-2-(2-hydroxyethyl)-1-pyrazolio]-methyl-3-cephem-4-carboxylate (syn isomer) (0.43 g).

IR (Nujol): 3300, 1770, 1640 cm$^{-1}$

NMR (DMSO-$d_6$, δ): 3.00 and 3.30 (2H, ABq, J=18 Hz), 3.60 (2H, m), 3.83 (3H, s), 4.37 (2H, m), 5.06 (1H, d, J=5 Hz), 5.18 (2H, broad s), 5.65 (1H, dd, J=5 Hz and 8 Hz), 5.84 (1H, d, J=3 Hz), 6.71 (1H, s), 7.18 (2H, broad s), 7.38 (2H, broad s), 8.08 (1H, d, J=3 Hz), 9.52 (1H, d, J=8 Hz).

The following compound (Example 5) was prepared according to a similar manner to that of Example 4.

EXAMPLE 5

(7β-[2-(2-Aminothiazol-4-yl)-2-(difluoromethoxyimino)acetamido]-3-[3-amino-2-(2-hydroxyethyl)-1-pyrazolio]methyl-3-cephem-4-carboxylate (syn isomer)

IR (Nujol): 3300, 1760, 1660 cm$^{-1}$

EXAMPLE 6

To a suspension of benzhydryl 7β-[2-(difluoromethoxyimino)-2-(2-tritylaminothiazol-4-yl)acetamido]-3-chloromethyl-3-cephem-4-carboxylate (syn isomer) (5 g) and sodium iodide (0.856 g) in N,N-dimethylformamide (5 ml) was added 5-formamido-1-(2-formyloxyethyl)pyrazole (4.18 g) at ambient temperature. After being stirred for 24 hours, the mixture was poured into a mixture of ethyl acetate and water. The separated organic layer was washed with water and sodium chloride aqueous solution, dried over magnesium sulfate, and evaporated in vacuo. The residue was dissolved in tetrahydrofuran, and subjected to a column chromatography on an ion-exchange resin Amberlite IRA 400 ($CF_3COO^\ominus$ type) (Trademark: manufactured by Rohm and Haas Co.). The object compound was eluted with tetrahydrofuran, and evaporated in vacuo to give trifluoroacetic acid salt of benzhydryl 7β-[2-(difluoromethoxyimino)-2-(2-tritylaminothiazol-4-yl)acetamido]-3-[3-formamido-2-(2-formyloxyethyl)-1-pyrazolio]methyl-3-cephem-4-carboxylate (syn isomer) (4.80 g).

IR (Nujol): 1780, 1720, 1675 cm$^{-1}$

NMR (DMSO-$d_6$, δ): 3.50 (2H, m), 3.65 (2H, m), 4.35 (2H, m), 5.25 (1H, d, J=5 Hz), 5.50 (2H, broad s), 5.88 (1H, dd, J=5 Hz and 8 Hz), 6.91 (1H, s), 7.03 (1H, s), 7.04–7.70 (27H, m), 8.08 (1H, s), 8.33 (1H, d, J=3 Hz), 8.67 (1H, s), 9.05 (1H, s), 10.05 (1H, d, J=5 Hz)

The following compound (Example 7) was obtained according to a similar manner to that of Example 6.

EXAMPLE 7

7β-[2-(2-Aminothiazol-4-yl)-2-methoxyiminoacetamido]-3-[3-amino-2-(2-hydroxyethyl)-1-pyrazolio]methyl-3-cephem-4-carboxylate (syn isomer)

IR (Nujol): 3300, 1770, 1640 cm$^{-1}$

EXAMPLE 8

To a solution of trifluoroacetic acid salt of benzhydryl 7β-[2-(difluoromethoxyimino)-2-(2-tritylaminothiazol-4-yl)acetamido]-3-[3-formamido-2-(2-formyloxyethyl)-1-pyrazolio]methyl-3-cephem-4-carboxylate (syn isomer) (4.7 g) in methylene chloride (15 ml) and anisole (5 ml) was added trifluoroacetic acid (10 ml) under ice-cooling. After being stirred for 1.5 hours, the mixture was poured into diisopropyl ether, and the resultant precipitate was collected by filtration. The precipitate was dissolved in water, adjusted to pH 12 with 1N sodium hydroxide aqueous solution under ice-cooling. The mixture was stirred at the same temperature for 10 minutes, and adjusted to pH 2 with 1N hydrochloric acid solution. This solution was subjected to a column chromatography on macroporous non-ionic adsorption resin "Diaion HP-20". The object compound was eluted with 10% diisopropyl alcohol, and lyophilized to give 7β-[2-(2-aminothiazol-4-yl)-2-(difluoromethoxyimino)acetamido]-3-[3-formamido-2-(2-hydroxyethyl)-1-pyrazolio]-methyl-3-cephem-4-carboxylate (syn isomer) (0.80 g).

IR (Nujol): 3250, 1770, 1665 cm$^{-1}$

NMR ($D_2O$ and DMSO-$d_6$, δ): 3.11 and 3.50 (2H, ABq, J=18 Hz), 3.85 (2H, m), 4.60 (2H, m), 5.22 (1H, d, J=5 Hz), 5.36 (2H, broad s), 5.81 (1H, d, J=5 Hz), 6.91 (1H, t, J=71 Hz), 7.05 (1H, d, J=3 Hz), 7.18 (1H, s), 8.24 (1H, d, J=3 Hz), 8.44 (1H, s)

EXAMPLE 9

To a suspension of 7β-[2-(2-aminothiazol-4-yl)-2(difluoromethoxyimino)acetamido]-3-[3-formamido-2-(2-hydroxyethyl)-1-pyrazolio]methyl-3-cephem-4-carboxylate (syn isomer) (0.7 g) in methanol (3.5 ml) was added concentrated hydrochloric acid (0.42 ml) at ambient temperature. After being stirred at the same temperature for 2 hours, the mixture was poured into ethyl acetate. The resulting precipitate was collected by filtration. The precipitate was dissolved in water, and adjusted to pH 2 with 5% aqueous sodium bicarbonate solution. This solution was subjected to a column chromatography on macroporous non-ionic adsorption resin "Diaion HP20". The object compound was eluted with 10% diisopropyl alcohol, and lyophilized to give 7β-[2-(2-aminothiazol-4-yl)-2-(difluoromethoxyimino)acetamido]-3-[3-amino-2-(2-hydroxyethyl)-1-pyrazolio]methyl-3-cephem-4-carboxylate (syn isomer) (0.41 g).

IR (Nujol): 3300, 1760, 1660 cm$^{-1}$

NMR (D$_2$O, δ): 3.02 and 3.35 (2H, ABq, J=18 Hz), 3.78 (2H, m), 4.28 (2H, m), 4.95 and 5.16 (2H, ABq, J=16 Hz), 5.16 (1H, d, J=5 Hz), 5.76 (1H, d, J=5 Hz), 5.92 (1H, d, J=3 Hz), 6.86 (1H, t, J=69 Hz), 7.16 (1H, s), 7.83 (1H, d, J=3 Hz)

The following compound (Example 10) was obtained according to a similar manner to that of Example 9.

EXAMPLE 10

7β-[2-(2-Aminothiazol-4-yl)-2-methoxyiminoacetamido]-3-[3-amino-2-(2-hydroxyethyl-1-pyrazolio]methyl-3-cephem-4-carboxylate (syn isomer)

IR (Nujol): 3300, 1770, 1640 cm$^{-1}$

EXAMPLE 11

To a solution of 7β-[2-(2-aminothiazol-4-yl)-2-methoxyiminoacetamido]-3-[3-amino-2-(2-hydroxyethyl)-1-pyrazolio]methyl-3-cephem-4-carboxylate (syn isomer) (6.5 g) in water (6.5 ml) was added 2N-sulfuric acid (6.5 ml) at room temperature. The mixture was stirred at room temperature to precipitate crystals. The crystals were collected by filtration and washed with ice-water and then acetone to give sulfuric acid salt of 7β-[2-(2-aminothiazol-4-yl)-2-methoxyiminoacetamido]-3-[3-amino-2-(2-hydroxyethyl)-1-pyrazolio]methyl-3-cephem-4-carboxylate (syn isomer)(5.92 g.

NMR (DMSO-d$_6$, δ); 3.13–3.83 (2H, m), 3.40–3.83 (4H, m), 5.15 (1H, d, J=5 Hz), 5.05 and 5.30 (2H, ABq, J=13 Hz), 5.79 (1H, d-d, J=5 Hz and 8 Hz), 5.88 (1H, d, J=3 Hz), 6.71 (1H, s), 7.28 (2H, broad s), 7.95 (1H, d, J=3 Hz), 9.57 (1H, d, J=8 Hz)

Preparation 5

7β-Amino-3-[3-amino-2-(2-hydroxyethyl)-1-pyrazolio]methyl-3-cephem-4-carboxylate trihydrochloride (66 g) was dissolved in water (264 ml). The aqueous solution was subjected to column chromatography on "Diaion HP-20" using water as eluent. Fractions containing the object compound were combined and to this combined solution was added dropwise isopropyl alcohol (1.15 l) under ice-cooling. The mixture was stirred for 1.5 hours under ice-cooling to precipitate crystals. The crystals were collected by filtration and washed with a mixture of isopropyl alcohol and water (10:1) under ice-cooling and dried over phosphorus pentoxide to give 7β-amino-3-[3-amino-2-(2hydroxyethyl)-1-pyrazolio]methyl-3-cephem-4-carboxylate.hydrochloride.dihydrate (29.95 g).

IR (Nujol): 3270, 1790, 1560–1635 cm$^{-1}$

NMR (DMSO-d$_6$, δ): 3.43–3.77 (2H, m), 4.47–5.07 (4H, m), 5.07 (1H, d, J=5 Hz), 5.12 and 5.38 (2H, ABq, J=16 Hz), 5.92 (1H, d, J=3 Hz), 7.56 (2H, broad s), 8.11 (1H, d, J=3 Hz).

Analysis (%) Calcd. for C$_{13}$H$_{17}$N$_5$O$_4$S.HCl.2H$_2$O: C:37.90, H:5.38,N:17.00, Cl:8.60: Found: C:37.82 H:5.56,N:16.73, Cl:8.60.

Preparation 6

A mixture of acetic anhydride (44.5 ml) and formic acid (22.3 ml) was stirred at room temperature for an hour. To this mixture was added 5-amino-1-(2-hydroxyethyl)pyrazole (30 g) at 0°–10° C., and the mixture was stirred under ice-cooling for 30 minutes. The mixture was poured into ice-cooled water, adjusted to pH 10.5 with 40% potassium carbonate solution, and stirred under ice-cooling for 30 minutes. The mixture was extracted with a mixture of tetrahydrofuran and ethyl acetate 6 times. The organic layer was dried over magnesium sulfate, and evaporated in vacuo to give 5-formamido-1-(2-hydroxyethyl)pyrazole (30.8 g).

mp: 109°–112° C.

IR (Nujol): 3230, 1695, 1570, 1540 cm$^{-1}$

NMR (DMSO-d$_6$, δ): 3.62–3.95 (2H, m), 3.98–4.32 (2H, m), 6.22 and 6.36 (1H, each d, J=3 Hz), 7.42 (1H, d, J=3 Hz), 8.32 and 8.36 (1H, each s).

Preparation 7

To a suspension of 5-formamido-1-(2-hydroxyethyl)pyrazole (1 g) in acetonitrile (50 ml) was added dropwise chlorosulfonyl isocyanate (0.77 ml) at −15° C.~−20° C. The mixture was stirred for 3 hours under ice-cooling. To the reaction mixture was added water (1 ml) and kept to stand overnight. The solution was adjusted to pH 7.5 with 5N-sodium hydroxide solution and then adjusted to pH 8.5 with 1N-sodium hydroxide solution. The organic layer was separated and the aqueous layer was extracted with tetrahydrofuran. The extract and said organic layer were combined and dried over magnesium sulfate. The solvent was distilled off and the residue was crystallized from ethyl acetate to give 5-amino-1-(2-carbamoyloxyethyl)pyrazole (0.60 g).

NMR (DMSO-d$_6$, δ): 3.83–4.35 (4H, m), 4.80–5.18 (2H, broad s), 5.32 (1H, d, J=3 Hz), 6.33–6.87 (2H, broad s), 7.08 (1H, d, J=3 Hz).

Preparation 8

5-Formamido-1-(2-carbamoyloxyethyl)pyrazole (3.69 g) was obtained from 5-amino-1-(2-carbamoyloxyethyl)pyrazole (3.3 g) according to a similar manner to that of Preparation 6.

NMR (DMSO-d$_6$, δ): 4.22 (4H, s), 6.17–6.40 (1H, m), 6.40–6.63 (2H, m), 7.30–7.53 (1H, m), 8.13–8.47 (1H, m).

EXAMPLE 12

To a solution of benzhydryl 7β-[2-(2-formamidothiazol-4-yl)-2-methoxyiminoacetamido]-3-chloromethyl-3-cephem-4carboxylate (syn isomer)(1.5 g) in N,N-dimethylformamide (3 ml) was added sodium iodide (0.36 g) under nitrogen atmosphere. The mixture was stirred at room temperature for 30 minutes. Then, 5-formamido-1-(2-carbamoyloxyethyl)pyrazole (1.42 g) was added thereto and the mixture was stirred at the same temperature for 24 hours. To the reaction mixture was added a mixture of ethyl acetate (50 ml) and ice-water (30 ml). The separated organic layer was washed with water and sodium chloride aqueous solution, and dried over magnesium sulfate. The solvent was evaporated in vacuo to give benzhydryl 7β-[2-(2-formamidothiazol-4-yl)-2-methoxyiminoacetamido]-3[3-formamido-2-(2-carbamoyloxyethyl)-1-pyrazolio]methyl-3-cephem-4-carboxylate trifluoroacetate (syn isomer) (1.60 g).

EXAMPLE 13

7β-[2-(2-Formamidothiazol-4-yl)-2-methoxyiminoacetamido]-3-[3-formamido-2-(2-carbamoyloxyethyl)-1-pyrazolio]methyl-3-cephem-4-carboxylate (syn isomer)(1.10 g) was obtained from benzhydryl 7β-[2-(2-formamidothiazol-4-yl)-2-methoxyiminoacetamido]-3-[3-formamido-2-(2-carbamoyloxyethyl)-1-pyrazolio]methyl-3-cephem-4-carboxylate trifluoroacetate (syn isomer)(1.6 g) according to a similar manner to that of Example 8.

EXAMPLE 14

7β-[2-(2-Aminothiazol-4-yl)-2-methoxyiminoacetamido]-3-[3-amino-2-(2-carbamoyloxyethyl)-1-pyrazolio]methyl-3-cephem-4-carboxylate (syn isomer)(0.10 g) was obtained from 7β-[2-(2-formamidothiazol-4-yl)-2-methoxyiminoacetamido]-3-[3-formamido-2-(2-carbamoyloxyethyl)-1-pyrazolio]methyl-3-cephem-4-carboxylate (syn isomer) according to a similar manner to that of Example 9.

IR (Nujol): 3200–3300, 1760, 1710, 1650 cm$^{-1}$

NMR (DMSO-$d_6$, δ): 3.0–3.90 (2H, m), 3.90–4.27 (4H, m), 3.82 (3H, s), 4.40–5.47 (5H, m), 5.47–5.77 (1H, m), 5.81 (1H, d, J=3 Hz), 6.71 (1H, s), 6.90–7.57 (4H, m), 7.97 (1H, d, J=3 Hz), 9.51 (1H, d, J=8 Hz).

Preparation 9

5-Formamido-4-methyl-1-(2-formyloxyethyl)-pyrazole was prepared according to a similar manner to that of Preparation 1.

IR (Nujol): 3180, 1715, 1660 cm$^{-1}$

NMR (DMSO-$d_6$, δ): 1.81 and 1.86 (3H, each s), 4.01–4.48 (4H, m), 7.25 and 7.40 (1H, each s), 8.06 (1H, s), 8.22 and 9.13 (1H, each s)

Preparation 10

5-Amino-1-(2-hydroxyethyl)pyrazole (5 g) was added to acetic anhydride (14.7 ml) with stirring and ice-cooling. Pyridine (6.3 ml) was added thereto. The mixture was stirred for 2 hours at 25° C.

The reaction mixture was added to a mixture of ethyl acetate (50 ml) and sodium chloride aqueous solution (50 ml). Then, an aqueous solution of sodium bicarbonate was added thereto to adjust the solution to pH 7.0. The aqueous layer was extracted with mixture of ethyl acetate and tetrahydrofuran. The extract was dried over magnesium sulfate. The magnesium sulfate was filtered off, and the filtrate was evaporated under reduced pressure to give 5-acetamido-1-(2-acetoxyethyl)pyrazole (5.98 g).

mp: 83°–84° C.

IR (Nujol): 3270, 1750, 1670, 1565 cm$^{-1}$

NMR (DMSO-$d_6$, δ): 1.93 (3H, s), 2.03 (3H, s), 4.22 (4H, br s), 6.13 (1H, d, J=2 Hz), 7.32 (1H, d, J=2 Hz), 9.76 (1H, s)

The following compounds (Preparations 11 to 13) were prepared according to a similar manner to that of Preparation 2.

Preparation 11

Benzhydryl 7β-tert-butoxycarbonylamino-3-[4-methyl-3-formamido-2-(2-formyloxyethyl)-1-pyrazolio]-methyl-3-cephem-4-carboxylate iodide IR (Nujol): 3250, 1780, 1710, 1680 cm$^{-1}$ NMR (DMSO-$d_6$, δ): 1.53 (9H, s), 1.97 (3H, s), 3.51 (2H, broad s), 4.04–4.42 (2H, m), 4.52–4.78 (2H, m), 5.08 (1H, d, J=5 Hz), 5.39 (2H, broad s), 5.61 (1H, dd, J=5 Hz and 8 Hz), 6.86 (1H, s), 7.08–7.52 (10H, m), 7.93 (1H, s), 8.18 (1H, s), 8.34 (1H, s), 9.12 (1H, s)

Preparation 12

Benzhydryl 7β-tert-butoxycarbonylamino-3-[3-acetamido-2-(2-acetoxyethyl)-1-pyrazolio]methyl-3-cephem-4-carboxylate iodide IR (Nujol): 1780, 1720, 1230 cm$^{-1}$ NMR (DMSO-$d_6$, δ): 1.41 (9H, s), 1.86 (3H, s), 2.25 (3H, s), 3.40 (2H, br s), 4.0–4.4 (4H, m), 5.12 (1H, d, J=5 Hz), 5.37 (2H, s), 5.60 (1H, dd, J=8 Hz and 5 Hz), 6.85 (1H, s), 7.24 (1H, d, J=3 Hz), 7.1–7.6 (10H, m), 7.90 (1H, d, J=8 Hz), 8.21 (1H, d, J=3 Hz), 11.17 (1H, s)

Preparation 13

Benzhydryl 7β-tert-butoxycarbonylamino-3-[3-formamido-2-(2-hydroxyethyl)-1-pyrazolio]methyl-3-cephem-4-carboxylate iodide IR (Nujol): 3300, 1780, 1710, 1560, 1150 cm$^{-1}$ NMR (DMSO-$d_6$, δ): 1.43 (9H, s), 3.53 (2H, br s), 4.0–4.5(4H,m), 5.15 (1H, d, J=5 Hz), 5.40 (2H, s), 5.55 (1H, dd, J=8 Hz and 5 Hz), 6.90 (1H, s), 7.01 (1H, d, J=3 Hz), 7.1–7.5 (10H, m), 7.97 (1H, d, J=8 Hz), 8.28 (1H, d, J=3 Hz), 8.50 (1H, s)

The following compounds (Preparations 14 to 16) were prepared according to a similar manner to that of Preparation 3.

Preparation 14

Bis(trifluoroacetic acid salts) of 7β-amino-3-[4-methyl-3-formamido-2-(2-formyloxyethyl)-1-pyrazolio]-methyl-3-cephem-4-carboxylate IR (Nujol): 1780, 1710, 1670 cm$^{-1}$ NMR (DMSO-$d_6$, δ): 1.98 (3H, s), 3.49 (2H, broad s), 4.22–4.48 (2H, m), 4.61–4.87 (2H, m), 5.18 (2H, broad s), 5.46 (2H, broad s), 8.05 (1H, s), 8.23 (1H, s), 8.35 (1H, s)

Preparation 15

Bis(trifluoroacetic acid salts) of 7β-amino-3-[3-acetamido-2-(2-acetoxyethyl)-1-pyrazolio]methyl-3-cephem-4-carboxylate IR (Nujol): 1780, 1660, 1190 cm$^{-1}$ NMR (DMSO-$d_6$, δ): 1.95 (3H, s), 2.23 (3H, s), 3.46 (2H, broad s), 4.1–4.4 (4H, m), 5.20 (2H, m), 5.46 (2H, s), 7.01 (1H, d, J=3 Hz), 8.27 (1H, d, J=3 Hz), 11.17 (1H, s)

Preparation 16

Bis(trifluoroacetic acid salts) of 7β-amino-3-[3-formamido-2-(2-hydroxyethyl)-1-pyrazolio]methyl-3-cephem-4-carboxylate IR (Nujol): 3400, 1780, 1680, 1580, 1200, 1140 cm$^{-1}$ NMR (DMSO-$d_6$, δ): 3.70 (2H, broad s), 4.2–4.7 (4H, m), 5.23 (2H, m), 5.50 (2H, s), 7.07 (1H, d, J=3 Hz), 8.35 (1H, d, J=3 Hz), 8.53 (1H, s)

The following compounds (Preparations 17 and 18) were prepared according to a similar manner to that of Preparation 4.

Preparation 17

7β-Amino-3-[4-methyl-3-amino-2-(2-hydroxyethyl)-1-pyrazolio]methyl-3-cephem-4-carboxylate trihydrochloride NMR (DMSO-$d_6$, δ): 1.94 (3H, s), 3.39 (2H, broad s), 3.47–3.78 (2H, m), 4.06–4.42 (2H, m), 5.21 (4H, broad s), 7.87 (1H, s)

Preparation 18

7β-Amino-3-[3-amino-2-(2-hydroxyethyl)-1-pyrazolio]methyl-3-cephem-4-carboxylate trihydrochloride IR (Nujol): 3300, 3150, 1780, 1710, 1640, 1580 cm$^{-1}$
NMR (DMSO-$d_6$, δ): 3.60 (2H, br s), 4.1–4.5 (4H, m), 5.23 (2H, m), 5.30 (2H, s), 5.92 (1H, d, J=3 Hz), 8.07 (1H, d, J=3 Hz)

The following compounds (Examples 15 to 18) were prepared according to a similar manner to that of Example 1.

EXAMPLE 15

7β-[2-(2-Formamidothiazol-4-yl)-2-methoxyiminoacetamido]-3-[4-methyl-3-amino-2-(2-hydroxyethyl)-1-pyrazolio]methyl-3-cephem-4-carboxylate (syn isomer)

IR (Nujol): 3150, 1770, 1650 cm$^{-1}$
NMR (DMSO-$d_6$, δ): 1.94 (3H, s), 3.32 (2H, broad s), 3.52–3.68 (2H, m), 3.88 (3H, s), 4.12–4.39 (2H, m), 5.14 (2H, broad s), 5.19 (1H, d, J=5 Hz), 5.82 (1H, dd, J=5 Hz and 8 Hz), 7.36 (1H, s), 7.83 (1H, s), 8.47 (1H, s), 9.63 (1H, d, J=8 Hz)

EXAMPLE 16

7β-[2-(2-Formamidothiazol-4-yl)-2-methoxyiminoacetamido]-3-[3-acetamido-2-(2-acetoxyethyl)-1-pyrazolio]methyl-3-cephem-4-carboxylate (syn isomer)

IR (Nujol): 1780, 1660, 1550 cm$^{-1}$
NMR (DMSO-$d_6$, δ): 1.96 (3H, s), 2.27 (3H, s), 3.2–3.6 (2H, m), 3.87 (3H, s), 4.1–4.5 (4H, m), 5.22 (1H, d, J=5 Hz), 5.43 (2H, s), 5.90 (1H, dd, J=8 Hz and 5 Hz), 7.00 (1H, d, J=3 Hz), 7.33 (1H, s), 8.29 (1H, d, J=3 Hz), 8.43 (1H, s), 9.62 (1H, d, J=8 Hz)

EXAMPLE 17

7β-[2-(2-Aminothiazol-4-yl)-2-methoxyiminoacetamido]-3-[4-methyl-3-amino-2-(2-hydroxyethyl)-1-pyrazolio]methyl-3-cephem-4-carboxylate (syn isomer)

IR (Nujol): 3300, 1765, 1660, 1605 cm$^{-1}$

EXAMPLE 18

7β-[2-(2-Aminothiazol-4-yl)-2-methoxyiminoacetamido]-3-[3-acetamido-2-(2-hydroxyethyl)-1-pyrazolio]methyl-3-cephem-4-carboxylate (syn isomer)

IR (Nujol): 3200, 1770, 1600 cm$^{-1}$

EXAMPLE 19

7β-[2-(2-Aminothiazol-4-yl)-2-methoxyiminoacetamido]-3-[4-methyl-3-amino-2-(2-hydroxyethyl)-1-pyrazolio]-methyl-3-cephem-4-carboxylate (syn isomer) was prepared according to a similar manner to that of Example 4.

IR (Nujol): 3300, 1765, 1660, 1605 cm$^{-1}$
NMR (D$_2$O, δ): 1.97 (3H, s), 3.06 and 3.37 (2H, ABq, J=18 Hz), 3.73–3.93 (2H, m), 3.98 (3H, s), 4.19–4.43 (2H, s), 5.09 (2H, broad s), 5.19 (1H, d, J=5 Hz), 5.89 (1H, d, J=5 Hz), 6.96 (1H, s), 7.71 (1H, s)

EXAMPLE 20

To a suspension of 7β-[2-(2-formamidothiazol-4-yl)-2-methoxyiminoacetamido]-3-[3-acetamido-2-(2-acetoxyethyl)-1-pyrazolio]methyl-3-cephem-4-carboxylate (syn isomer) (1.46 g) in methanol (7.3 ml) was added conc. hydrochloric acid (0.51 ml) at room temperature. The mixture was stirred for 5 hours at room temperature.

The reaction mixture was added to ethyl acetate with stirring and ice-cooling. The produced amorphous solid was dried in vacuo, and it was dissolved in water (40 ml). The aqueous solution was adjusted to pH 13 with 1N sodium hydroxide aqueous solution with stirring at −3°~0° C., and stirred for 2 hours at the same temperature. The aqueous solution was adjusted to pH 2 with 1N hydrochloric acid, and subjected to column chromatography on "Diaion HP-20" and eluted with 10% aqueous isopropyl alcohol. The fractions containing the object compound were combined and concentrated to remove isopropyl alcohol, and lyophilized to give 7β-[2-(2-aminothiazol-4-yl)-2-methoxyiminoacetamido]-3-[3-acetamido-2-(2-hydroxyethyl)-1-pyrazolio]methyl-3-cephem-4-carboxylate (syn isomer) (159 mg).

mp: 160° C. (dec.)
IR (Nujol): 3200, 1770, 1600 cm$^{-1}$
NMR (D$_2$O, δ): 2.26 (3H, s), 3.10 (1H, d, J=18 Hz), 3.47 (1H, d, J=18 Hz), 3.8–4.1 (4H, m), 3.95 (3H, s), 5.20 (1H, d, J=5 Hz), 5.32 (2H, s), 5.77 (1H, d, J=5 Hz), 6.93 (1H, d, J=3 Hz), 6.94 (1H, s), 8.16 (1H, d, J=3 Hz)

The following compounds (Examples 21 and 22) were prepared according to a similar manner to that of Example 6.

EXAMPLE 21

7β-[2-(2-Aminothiazol-4-yl)-2-methoxyiminoacetamido]-3-[4-methyl-3-amino-2-(2-hydroxyethyl)-1-pyrazolio]methyl-3-cephem-4-carboxylate (syn isomer)

IR (Nujol): 3300, 1765, 1660, 1605 cm$^{-1}$

EXAMPLE 22

7β-[2-(2-Aminothiazol-4-yl)-2-methoxyiminoacetamido]-3-[3-acetamido-2-(2-hydroxyethyl)-1-pyrazolio]methyl-3-cephem-4-carboxylate (syn isomer)

IR (Nujol): 3200, 1770, 1600 cm$^{-1}$

The following compounds (Examples 23 to 27) were prepared according to a similar manner to that of Example 8.

EXAMPLE 23

7β-[2-(2-Aminothiazol-4-yl)-2-methoxyiminoacetamido]-3-[3-amino-2-(2-hydroxyethyl)-1-pyrazolio]-methyl-3-cephem-4-carboxylate (syn isomer)

IR (Nujol): 3300, 1770, 1640 cm$^{-1}$

EXAMPLE 24

7β-[2-(2-Aminothiazol-4-yl)-2-(difluoromethoxyiminoacetamido]-3-[3-amino-2-(2-hydroxyethyl)-1pyrazolio]-methyl-3-cephem-4-carboxylate (syn isomer)

IR (Nujol): 3300, 1760, 1660 cm$^{-1}$

EXAMPLE 25

7β[2-(2-Aminothiazol-4-yl)-2-methoxyiminoacetamido]-3-[3-amino-2-(2-carbamoyloxyethyl)-1-pyrazolio]methyl-3-cephem-4-carboxylate (syn isomer)

IR (Nujol): 3200–3300, 1760, 1710, 1650 cm$^{-1}$

EXAMPLE 26

7β-[2-(2-Aminothiazol-4-yl)-2-methoxyiminoacetamido]-3-[4-methyl-3-amino-2-(2-hydroxyethyl)-1-pyrazolio]methyl-3-cephem-4-carboxylate (syn isomer)

IR (Nujol): 3300, 1765, 1660, 1605 cm$^{-1}$

EXAMPLE 27

7β-[2-(2-Aminothiazol-4-yl)-2-methoxyiminoacetamido]-3-[3-acetamido-2-(2-hydroxyethyl)-1-pyrazolio]methyl-3-cephem-4-carboxylate (syn isomer)

IR (Nujol): 3200, 1770, 1600 cm$^{-1}$

What we claim is:

1. A cephem compound of the formula:

wherein
 $R^6$ is amino or a protected amino,
 $R^2$ is lower alkyl which may have 1 to 3 halogens,
 $R^3$ is COO$^\ominus$, carboxy or a protected carboxy,
 $R^4$ is hydroxy(lower)alkyl or protected hydroxy(lower)alkyl,
 $R^5$ is amino or a protected amino,
 $R^6$ is hydrogen or lower alkyl,
 $X^\ominus$ is an anion, and
 n is 0 or 1,
with proviso that
 (i) when $R^3$ is COO$^\ominus$, then n is 0, and
 (ii) when $R^3$ is carboxy or a protected carboxy, then n is 1,
and pharmaceutically acceptable salt thereof.

2. A compound of claim 1, wherein
 $R^1$ is amino, ar(lower)alkylamino or lower alkanoylamino,
 $R^2$ is lower alkyl which may have 1 to 3 halogen,
 $R^3$ is COO$^\ominus$, carboxy or ar(lower)alkoxycarbonyl,
 $R^4$ is hydroxy(lower)alkyl, lower alkanoyloxy(lower)alkyl or carbamoyloxy(lower)alkyl, and
 $R^5$ is amino or lower alkanoylamino.

3. A compound of claim 2, wherein
 $R^1$ is amino, and
 $R^3$ is COO$^\ominus$ or carboxy.

4. A compound of claim 3, wherein
 $R^2$ is lower alkyl or dihalo(lower)alkyl.

5. A compound of claim 4, wherein
 $R^2$ is methyl or difluoromethyl,
 $R^4$ is 2-hydroxyethyl, 2-formyloxyethyl, 2-acetoxyethyl or 2-carbamoyloxyethyl,
 $R^5$ is amino, formamido or acetamido, and
 $R^6$ is hydrogen or methyl.

6. A compound of claim 5, which is 7β-[2-(2-aminothiazol-4-yl)-2-methoxyiminoacetamido]-3-[3-amino-2-(2-hydroxyethyl)-1-pyrazolio]methyl-3-cephem-4-carboxylate (syn isomer) or its sulfuric acid salt.

7. An antimicrobial pharmaceutical composition which comprises, as an active amount of a compound of claim 1 or a pharmaceutically acceptable salt thereof in admixture with a pharmaceutically acceptable carrier.

8. A method for the treatment of infectious diseases which comprises administering an effective amount of a compound of claim 1 or a pharmaceutically acceptable salt thereof to a human or animal.

* * * * *